(12) United States Patent
Brighton et al.

(10) Patent No.: US 6,983,643 B2
(45) Date of Patent: Jan. 10, 2006

(54) GROUND ASSESSMENT

(75) Inventors: James Laurent Brighton, Norwich (GB); Richard John Godwin, Silsoe (GB)

(73) Assignee: Cranfield University, Silsoe (GB)

( * ) Notice: Subject to any disclaimer, the term of this patent is extended or adjusted under 35 U.S.C. 154(b) by 0 days.

(21) Appl. No.: 10/416,518

(22) PCT Filed: Nov. 26, 2001

(86) PCT No.: PCT/GB01/05210

§ 371 (c)(1),
(2), (4) Date: Dec. 23, 2003

(87) PCT Pub. No.: WO02/42738

PCT Pub. Date: May 30, 2002

(65) Prior Publication Data

US 2004/0079141 A1    Apr. 29, 2004

(30) Foreign Application Priority Data

Nov. 24, 2000  (GB) .................................. 0028645

(51) Int. Cl.
*G01N 3/48* (2006.01)
(52) U.S. Cl. ............................................. 73/81; 73/84
(58) Field of Classification Search ................... 73/84, 73/81, 11.01, 11.03, 85
See application file for complete search history.

(56) References Cited

U.S. PATENT DOCUMENTS

| 3,623,359 | A | * | 11/1971 | Kloc .............................. 73/84 |
| 4,302,967 | A | * | 12/1981 | Dufey ............................ 73/84 |
| 4,594,899 | A | * | 6/1986 | Henke et al. ................. 73/784 |
| 4,649,741 | A | | 3/1987 | Strom |
| 5,313,825 | A | | 5/1994 | Webster et al. |
| 5,337,613 | A | * | 8/1994 | Kovari ......................... 73/784 |
| 5,726,349 | A | | 3/1998 | Palmertree et al. |
| 6,531,965 | B1 | * | 3/2003 | Kaiser et al. ................. 73/84 |
| 6,701,771 | B2 | * | 3/2004 | Frost et al. ................... 73/84 |

FOREIGN PATENT DOCUMENTS

DE          198 06 903        9/1999

* cited by examiner

*Primary Examiner*—Thomas P. Noland
*Assistant Examiner*—Nashmiya Fayyaz
(74) *Attorney, Agent, or Firm*—Oblon, Spivak, McClelland, Maier & Neustadt, P.C.

(57) ABSTRACT

For assessing ground quality, such as a condition of a racetrack, a handheld device has a shaft, a plate mounted to its bottom end, and a sensor body also mounted to the bottom of the shaft, independently of the plate. A tine tip projects below the sensor body. The sensor body has compression sensors and shear sensors. The user pushes down on the shaft. The tine tip penetrates the ground until the plate abuts the surface. Continued pushing leads to a compression reading. The user then pushes the top of the shaft so that it tilts, pivoting about an edge of the plate. Shear forces are sensed by the shear sensors. The compression and shear data pass to a data processor that computes a single value indicative of the ground quality.

20 Claims, 2 Drawing Sheets

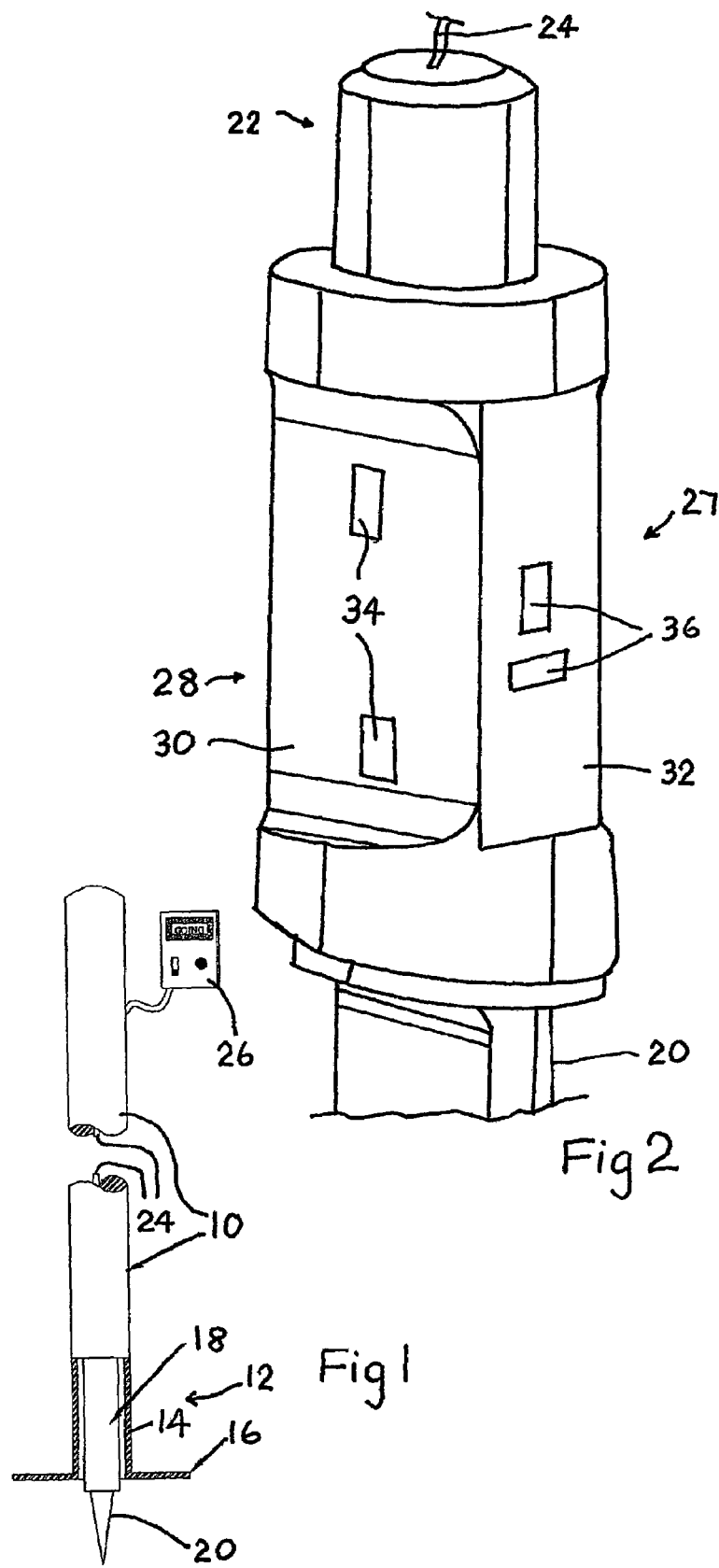

GROUND ASSESSMENT

TECHNICAL FIELD

The present invention relates to apparatus and methods for assessing the mechanical properties of soil such as the strength of the ground surface. It may be applied to assessing the load bearing properties and/or the ground's suitability for some purposes. A particular application is the assessment of the "going" of racecourses or, more generally, how the soil will affect attempted travel across it (vehicular, by animal or pedestrian) or how such activities will affect the ground.

The ability to determine the "going" of a racecourse is essential to the racing industry because the performance of a racehorse will be, to a large degree, dependant on the 'going' of the ground at the time of the race. The 'going' is a descriptor of the ground conditions on the course and ranges from heavy to hard. The soil conditions for harder 'going' will cause a horse to run faster but at an ever increasing risk of injury due to greater shock loads on impact with the surface. The opposite is true as the 'going' becomes heavier, with slower times and more effort required from the horse as the ground absorbs the impact energy.

BACKGROUND ART

At present the Clerk of each racecourse determines the 'going'. They will use their own experience and knowledge to classify the 'going' relating to their own observations of soil behaviour when moved with a wooden stick. This has the possibility of inconsistency across. racecourses due to differing approaches used by the Course Clerks.

DISCLOSURE OF INVENTION

We have appreciated that the 'going' is influenced by the shear strength of the soil, its resistance to penetration and its plastic/elastic response to an impact. Harder "going" corresponds to greater shear strength and penetration resistance, and lesser plastic deformation.

Improvements in the consistency, with which the 'going' can be measured irrespective of user and course, will be of a major benefit to the racing industry. In particular, trainers and owners will be able to have a consistent scale of 'going' on which to decide whether or not to run their horses. This will allow them to pick ideal conditions for their horse and also to ensure that the horse avoids injury by not running in inappropriate conditions. In addition, the invention will provide a more accurate indicator of course conditions, and can therefore help in the management of the course to optimise the 'going'.

In a first aspect there is provided a device for assessing the mechanical properties of soil comprising (i) a transverse element having a soil-engaging lower face; (ii) a soil penetrating element projecting downwardly beneath said lower face; (iii) means for urging said element selectively (a) to move downwardly into the soil and (b) to move with an angular motion so that one edge region rises while an opposite edge region descends or provides a fulcrum; and (iv) force sensing means for sensing (a) compression forces associated with said downward motion; and (b) shear forces associated with said angular motion.

In a second aspect there is provided a method of assessing the mechanical properties of soil comprising (a) measuring resistance to penetration; (b) measuring resistance to shear and (c) computing a single value indicative of soil properties. This preferably employs a device according to the first aspect.

A preferred type of embodiment is a handheld measurement device, typically comprising a tine tip, sensing unit, shaft, and signal processing and display unit. It preferably enables the determination of 'Going' by the measurement of soil penetration and soil shear in combination or individually. The sensor creates signals relating to the force system imposed on it by the ground. The use of a plate beneath the sensor enables the sensing unit to be independent of the user (when operated in the correct manner) and therefore creates a highly consistent measurement. An electronic circuit then converts the signals into one measure of 'going', which is then displayed to the user or logged for subsequent download to a computer.

In use, the tip of the device, when forced into the ground surface by the user applying a vertical load on the shaft, transmits a compression force to the sensing unit. The electronic circuitry collects signals from the sensing unit and converts them into a measure of penetration resistance. The user then applies a horizontal force to the top of the shaft, and the tip (which is still in the ground) transmits a moment to the sensing unit. The electronic circuitry collects the signals from the sensing unit and converts them into a measure of soil shear strength. The signal processor then combines these signals and applies a numerical relationship to convert the two signals to one measure of 'going'. This is then logged or displayed to the user.

Preferably the sensor is one physical unit comprising of a machined metal beam which forms the join between the tip, shaft and plate. Two sets of strain gauges may be bonded onto the beam in specific positions to make up the two independent sensing circuits, one for vertical penetration and one for shear.

The transverse element may comprise a plate. Its functions are (a) to control the depth of insertion during the vertical penetration, and to isolate the sensor from the user. The plate is connected directly to the shaft and not to the tip. In this manner, when the user inserts the stick into the ground, as long as the plate touches the ground, the measurement from the sensor taken when fully inserted will be almost entirely independent of the user's vertical force.

When taking the shear reading the plate acts as a pivot about which the shear movement is produced. Using the stick in this way creates soil/turf shear resistance which is measured by the sensor.

The signal processor may have two primary functions. Firstly it must collect the electrical signals from the sensor sequentially, penetration first, followed by shear. This data is then processed into information by combining the data from each measurement and comparing them with preset values to derive a numerical indication of the going, and the going class. The preset values are being investigated at present through a large test and evaluation program. Once the data have been gathered, a look up table or mathematical model will be derived and programmed into the signal processing unit to determine the going from the measurements taken. This will all be conducted digitally.

A device may be adapted to gather GPS data via a sensor mounted in the signal processor enclosure and combine it with the going assessment information. This will allow the simultaneous collection of going and position to enable the on-line construction of a going 'map' for the area being considered.

It should also be mentioned that although the device has been designed to provide a measure of 'Race Course Going' there may well be applications in other industries where the assessment of the strength of the surface layers of soils is important, for example Forestry, where vehicle mobility prediction is a crucial element of their work.

BRIEF DESCRIPTION OF DRAWINGS

FIG. 1 is a schematic view of a device embodying the invention.

FIG. 2 is a perspective view of the sensor unit of the device of FIG. 1.

BEST MODE FOR CARRYING OUT THE INVENTION

Figure 3:
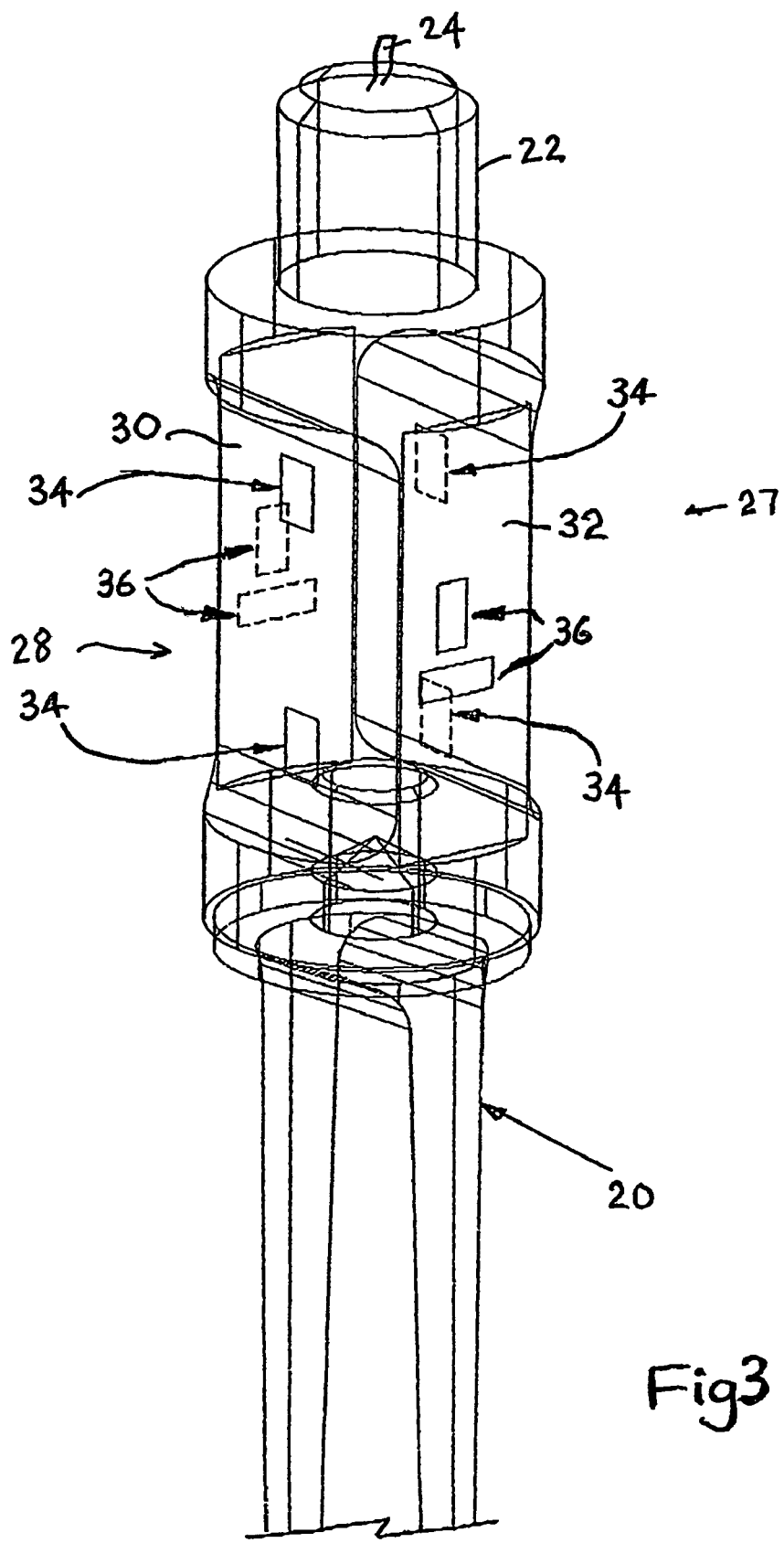
FIG. 3 is a view like that of FIG. 2 but showing hidden detail.

FIG. 1 shows a device having a long tubular rod-like shaft or handle 10 connected at its bottom end to a bush member 12 having a cylindrical tubular portion 14 ending in an out-turned flange 16 which constitutes a ground abutment plate. A sensor unit 18 fits mainly within the tubular portion 14. It is connected to, or integral with, a tine tip 20 which projects beneath the abutment plate 16.

The sensor unit is shown in more detail in FIGS. 2 and 3. It largely consists of a machined metal beam which interconnects the tine tip 20, the handle 10 and the bush member 12. An upper portion 22 of reduced diameter has an external screw thread for connection to an internal screw thread at the bottom end of the tubular handle 10. A cable 24 from the sensor unit extends up the handle interior and is connected to a display unit 26.

The main body portion 27 of the sensor beam has a central portion 28 of approximately square section, with two pairs 30,32 of outwardly directed faces. A first pair 30 bears four strain gauges 34, two on each face. They are disposed and connected in a differential cantilever configuration, being wired into a four-arm active Wheatstone bridge. The two gauges on each of these faces are symmetrically disposed, on the central vertical axis of the face, with the gauges on the two faces being in corresponding positions. They constitute a shear bridge, for measuring shear or moment.

The second pair of faces 32 also carry two strain gauges 36 each, wired into a four-arm active Wheatstone bridge. However they are disposed in a Poisson (compression) configuration. The two gauges 36 on each of the second faces are symmetrically disposed on the central vertical axis of the face, but with one gauge disposed transversely whereas the other is longitudinal. They constitute a penetration bridge, for sensing the compression forces associated with penetration down into the soil.

In use, the user holds the handle 10 and pushes down so that the tine tip penetrates the soil, until the plate 16 is in contact with the soil surface. The device is then ready to take a reading. Firstly, the user continues to push downwardly. The force on the shaft is transferred directly to the plate. The tine tip experiences forces as it is caused to penetrate deeper into the soil. The penetration bridge senses the forces. Data are sent to the display unit 26 which includes a signal processor.

Secondly the handle is pushed forwardly or rearwardly (at its top), so that the device tilts, pivotting about an edge of the plate 16. The tine tip 20 transmits shear forces, related to the turning movement, to the sensor unit, where they are sensed by the shear bridge. (The appropriate plane or planes of tilting depend on the arrangement of the shear sensors.) Once again, data are sent to the processor in the display unit 26. This analyses the data to produce an output indicative of the "going" properties of the ground surface region. The analysis may involve determining maximum values for the compression and shear data, and using an algorithm to derive a measure of 'going'. This may be logged and/or displayed.

What is claimed is:

1. A device for assessing properties of soil comprising:
a transverse element with a soil-engaging lower face;
a soil penetrating element projecting downwardly beneath said lower face;
means for urging said transverse element and said soil penetrating element selectively to move said soil penetrating element downwardly in a downward motion into the soil and to move said transverse element with an angular motion so that a first edge region of said transverse element rises while a second edge region opposite to the first edge region descends or provides a fulcrum for said angular motion;
force sensing means for sensing compression forces associated with said downward motion and shear forces associated with said angular motion; and
processing means coupled to said force sensing means for receiving data from said sensing means and for providing an output related to said properties of said soil.

2. A device according to claim 1, wherein said means for urging comprises an upwardly extending elongate shaft.

3. A device according to claim 2, wherein said transverse element is mounted on said shaft.

4. A device according to claim 2, wherein said force sensing means is interposed between said shaft and said soil penetrating element.

5. A device according to claim 4, wherein said transverse element is not directly connected to at least one of said sensing means and said soil penetrating element.

6. A device according to claim 1, wherein said force sensing means comprises a body coupled to the soil penetrating element and a plurality of strain gauges mounted to said body.

7. A device according to claim 6, wherein said strain gauges are arranged to form a differential cantilever set for sensing the shear forces and a compression sensing set.

8. A device according to claim 6, wherein the strain gauges are wired into a four-arm active wheatstone bridge.

9. A device according to claim 1, further comprising display means coupled to said processing means for displaying said output related to said soil properties.

10. A method of assessing properties of soil employing the device according to claim 1, comprising:
measuring a resistance to vertical penetration into said soil;
measuring a resistance to horizontal shear into said soil; and
combining the resistance to vertical penetration with the resistance to horizontal shear to obtain a measure indicative of soil properties for said soil.

11. A device according to claim 1, wherein said force sensing means comprises a square section with four outwardly directed faces.

12. A device according to claim 11, further comprising at least one strain gauge arranged on each of said outwardly directed faces.

13. A device according to claim 1, wherein said soil penetrating element is configured to penetrate said soil until said soil-engaging lower face of said transverse element engages a surface of said soil.

14. A device according to claim 1, wherein said properties provide an indication of going conditions for a horse.

15. A device for sensing properties of soil comprising:
a transverse element with a soil-engaging lower face;
a tip configured to project downwardly beneath said lower face to penetrate the soil;
an elongated shaft configured to urge said transverse element and said tip selectively to move said tip downwardly in a downward motion into the soil and to move said transverse element with an angular motion so that a first edge region of said transverse element rises while a second edge region opposite to said first region descends or provides a fulcrum for said angular motion; and
a sensor located between said tip and said elongated shaft, said sensor being configured to measure compression forces associated with said downward motion and shear forces associated with said angular motion.

16. A device according to claim 15, wherein said transverse element comprises a plate, directly connected to said shaft and not connected to said tip.

17. A device according to claim 15, further comprising:
a processor configured to convert a signal from said sensor into a value; and
a display configured to display said value.

18. A device according to claim 17, wherein said value provides information on the properties of said soil.

19. A device according to claim 17, further comprising a computer connected to said processor.

20. A device according to claim 17, further comprising a GPS receiver connected to said processor.

* * * * *